United States Patent [19]

Baillie et al.

[11] Patent Number: 4,780,473
[45] Date of Patent: Oct. 25, 1988

[54] BICYCLIC FUNGICIDES

[75] Inventors: Alister C. Baillie, Bottisham, England; Antony D. Buss, Berlin, Fed. Rep. of Germany; John H. Parsons, Saffron Walden; Philip E. Russell, Sawston, both of England

[73] Assignee: Schering Agrochemicals Ltd., Great Britain

[21] Appl. No.: 132,129

[22] Filed: Dec. 14, 1987

Related U.S. Application Data

[63] Continuation-in-part of Ser. No. 893,491, Aug. 5, 1986, abandoned.

[30] Foreign Application Priority Data

Aug. 8, 1985 [GB] United Kingdom ............... 8519920

[51] Int. Cl.[4] .................. A01N 43/52; A01N 57/32; C07D 235/30
[52] U.S. Cl. ...................... 514/395; 514/80; 514/81; 514/303; 546/23; 546/118; 548/111; 548/329
[58] Field of Search ............... 548/111, 329; 546/118, 546/23; 514/81, 80, 303, 395

[56] References Cited

U.S. PATENT DOCUMENTS 3,738,994  6/1973  Fisher ............... 548/329 X
4,197,307  4/1980  Gallay et al. ........ 548/329 X Primary Examiner—Richard A. Schwartz
Attorney, Agent, or Firm—Ostrolenk, Faber, Gerb & Soffen

[57] ABSTRACT

Compounds are disclosed having fungicidal activity and are of general formula I

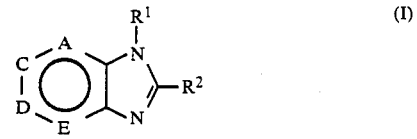

where at least three of A, C, D and E are —CX= and the other is —CX= or —N=, where X is hydrogen, $C_{1-8}$-alkyl (optionally substituted by halogen), halo, nitro or phenoxy, in which the phenyl is optionally substituted by one or more groups selected from halo and trifluoromethyl;
$R^1$ is —$SO_2R^3$ or

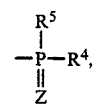

and
$R^2$ is

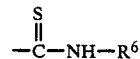

where $R^6$ is hydrogen, $C_{1-8}$-alkyl (optionally substituted by one or more groups selected from halogen and hydroxy), $C_{1-8}$-alkanoyl, benzoyl, cyclohexylcarbonyl or aminocarbonyl (in which the amino is substituted by benzoyl or chlorobenzenesulphonyl);
$R^3$, $R^4$, and $R^5$ may be the same or different and have the meanings given to $R^6$ or can be di-$C_{1-8}$-alkylamino; and Z is oxygen or sulphur; and when $R^1$ is

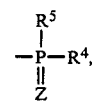

$R^2$ can also be —CN.

12 Claims, No Drawings

BICYCLIC FUNGICIDES

This application is a continuation-in-part of our application Ser. No. 893,491, filed Aug. 5 1986, now abandoned.

This invention relates to compounds having fungicidal activity.

In GB Patent Application No. 2114567, there are disclosed compounds having fungicidal activity which are of formula

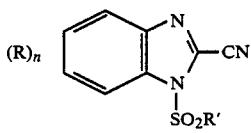

where R can represent various groups such as halogen or alkyl, n is 0 to 3 and R' is inter alia substituted amino.

We have now discovered that compounds of similar structure in which the cyano group and/or the sulphonyl group is replaced by different groups have particularly valuable properties.

According to the invention there is provided a compound of general formula I

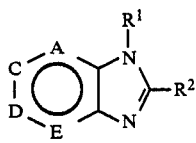

where at least three of A, C, D and E are —CX= and the other is —CX= or —N=, where X is hydrogen, $C_{1-8}$-alkyl (optionally substituted by halogen), halo, nitro or phenoxy, in which the phenyl is optionally substituted by one or more groups selected from halo and trifluoromethyl;

$R^1$ is —$SO_2R^3$ or

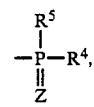

and
$R^2$ is

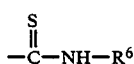

where
$R^6$ is hydrogen, $C_{1-8}$-alkyl (optionally substituted by one or more groups selected from halogen and hydroxy), $C_{1-8}$-alkanoyl, benzoyl, cyclohexylcarbonyl or aminocarbonyl (in which the amino is substituted by benzoyl or chlorobenzenesulphonyl);

$R^3$, $R^4$, and $R^5$ may be the same or different and have the meanings given to $R^6$ or can be di-$C_{1-8}$-alkylamino; and Z is oxygen or sulphur;

and when $R^1$ is $$\begin{matrix} R^5 \\ | \\ -P-R^4, \\ \| \\ Z \end{matrix}$$

$R^2$ can also be —CN.

Preferably all of A, C, D and E groups are —CX=. Each X can be the same or different. When one of the groups is =N—, this is generally A or E.

A preferred group of compounds is that in which $R^1$ is —$SO_2R^3$ and $R^2$ is —$CSNH_2$.

The compounds of the invention have activity as fungicides, especially against fungal diseases of plants, e.g. mildews, especially vine downy mildew (*Plasmopora viticola*). They are also active against powdery mildews such as barley powdery mildew (*Erysiphe graminis*), as well as being active against diseases such as rice blast (*Pyricularia oryzae*), wheat brown rust (*Puccinia recondita*) and late tomato blight and potato blight (*Phytophthora infestans*). They may also have activity against other diseases such as Fusarium spp. and *Pythium ultimum*.

The invention thus also provides a method of combating fungi at a locus infested or liable to be infested therewith, which comprises applying to the locus a compound of formula I.

The invention also provides an agricultural composition comprising a compound of formula I in admixture with an agronomically acceptable diluent or carrier.

The composition of the invention may of course include more than one compound of the invention.

In addition the composition can comprise one or more additional active ingredients, for example compounds known to possess plant-growth regulant, herbicidal, fungicidal, insecticidal or acaricidal properties. Alternatively, the compounds of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkyl-naphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively, it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to plants is preferably within the range of 0.01 to 3.0 percent by weight, especially 0.01 to 1.0 percent by weight. In a primary composition, the amount of active ingredient can vary widely and can be, for example, from 5 to 95 percent by weight of the composition.

In the method of the invention, the compound is generally applied to seeds, plants or their habitat. Thus, the compound can be applied directly to the soil before, at or after drilling so that the presence of active compound in the soil can control the growth of fungi which may attack seeds. When the soil is treated directly, the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.05 to 20 kg per hectare, more preferably from 0.1 to 10 kg per hectare.

Alternatively, the active compound can be applied directly to the plant by, for example, spraying or dusting either at the time when the fungus has begun to appear on the plant or before the appearance of fungus as a protective measure. In both such cases, the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant, a suitable rate of application is from 0.01 to 10 kg. per hectare, preferably from 0.05 to 5 kg per hectare.

The compounds of the invention may be prepared by reacting a compound of formula II

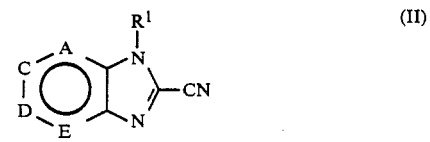

with hydrogen sulphide to give a compound where $R^6$ is hydrogen and if desired subsequently treating this with a compound of formula

where Q is hydrogen, a leaving group, such as halogen, or represents a bond forming a carbonyl group.

Compounds of formula I, where $R^2$ is —CN and $R^1$ is

can be prepared by treating the compound of formula II, where $R^1$ is hydrogen with a compound of formula

where Y is a leaving group such as halogen.

The invention is illustrated in the following Examples. Structures of isolated novel compounds were confirmed by elemental and/or other appropriate analyses. Temperatures are in °C.

EXAMPLE 1

Hydrogen sulphide was bubbled through a stirred suspension of 5,6-dichloro-1-(dimethylsulphamoyl)benzimidazole-2-carbonitrile (8.0 g) and triethylamine (2.5 g) in ethanol (200 ml). After 1 hour, the deep red solution was evaporated and the residue recrystallised from toluene to give 5,6-dichloro-1-(dimethylsulphamoyl)-benzimidazole-2-carbothioamide, m.p. 185–186. (Compound 1)

EXAMPLE 2

A suspension of the product of Example 1 (2.00 g) in a solution of anhydrous chloral (5.32 g) in dichloromethane (40 ml) was stirred and refluxed for 3 days. The yellow solid was filtered off and washed well with dichloromethane to give 5,6-dichloro-1-(dimethylsulphamoyl)-N-(1-hydroxy-2,2,2-trichloroethyl)benzimidazole-2-carbothioamide, m.p. 158°-160°. (Compound 2)

EXAMPLE 3

A solution of the product of Example 1 (3.20 g) and 2-chlorophenylsulphonyl isocyanate (2.25 g) in ethyl acetate (60 ml) was stirred at room temperature for 4 days. The precipitated yellow solid was filtered off and washed with ethyl acetate and dried in air to give 5,6-dichloro-1-(dimethylsulphamoyl)-N-(2-chlorophenylsulphonylcarbamoyl)benzimidazole-2-carbothioamide, m.p. 131°-2°. (Compound 3)

EXAMPLE 4

Acetyl chloride (1.57 g) was added dropwise at 0°-5° (ice-bath) to a stirred solution of the product of Example 1 (3.53 g) and pyridine (1.74 g) in acetone (25 ml). A solid began to separate and the resulting mixture was stirred and refluxed for 20 min and then evaporated in vacuo. The residue was partitioned between dichloromethane and water and the organic layer was separated, dried and evaporated. The major product was purified by flash chromatography using 5% methanol in dichloromethane as eluent and then recrystallised from toluene/cyclohexane (1:1) to give 5,6-dichloro-1-(dimethylsulphamoyl)-N-acetylbenzimidazole-2-carbothioamide, m.p. 172°-3°. (Compound 4)

EXAMPLE 5

A solution of the product of Example 1 (1.00 g) and aqueous formaldehyde (10 ml) in dioxane (40 ml) containing triethylamine (1 drop) was stirred at room temperature. The reaction mixture was diluted with cold water (100 ml) and extracted with ether (150 ml). The ether extract was washed four times with water (100 ml) and then dried and evaporated to give 5,6-dichloro-1-(dimethylsulphamoyl)-N-(hydroxymethyl)benzimidazole-2-carbothioamide, m.p. 140°-2°. (Compound 5).

EXAMPLE 6

In a similar manner to that described in one of the previous Examples, the following were obtained.

| Cpd | $R^3$ | $R^6$ | $(W)_n$ | m.p.(°) |
|---|---|---|---|---|
| 6 | $NMe_2$ | H | $5Br,4,6Cl_2$ | 203 |
| 7 | $NMe_2$ | H | $5/6Cl$ | 172-5 |
| 8 | $NMe_2$ | H | $4,5,6Cl_3$ | 204 |
| 9 | $NMe_2$ | H | $5/6NO_2$ | 159-63 |
| 10 | $NMe_2$ | H | $5Cl, 7$-aza*$/6Cl, 4$-aza | 300 |
| 11 | $NMe_2$ | H | $5/6(2Cl, 4CF_3$—PhO$)$ | 115-45 |
| 12 | $NMe_2$ | H | $5/6CF_3$ | 158-64 |
| 13 | $Pr^i$ | H | $5,6Cl_2$ | 193-4 |
| 14 | $NMe_2$ | $COPr^n$ | $5,6Cl_2$ | 173-5 |
| 15 | $NMe_2$ | COEt | $5,6Cl_2$ | 152-4 |
| 16 | $NMe_2$ | COPh | $5,6Cl_2$ | 166-8 |
| 17 | $NMe_2$ | $COC_5H_{11}{}^n$ | $5,6Cl_2$ | 165-9 |
| 18 | $NMe_2$ | COMe | $5/6NO_2$ | 140-50 |
| 19 | $NMe_2$ | $COC_7H_{15}{}^n$ | $5,6Cl_2$ | 120-4 |
| 20 | $NMe_2$ | $COPr^i$ | $5,6Cl_2$ | 170-2 |
| 21 | $NMe_2$ | $COBu^t$ | $5,6Cl_2$ | 173-6 |
| 22 | $NMe_2$ | $CH(OH)CCl_3$ | $5/6NO_2$ | 75-100 |
| 23 | $NMe_2$ | COcyclohexyl | $5,6Cl_2$ | 162-5 |
| 24 | $NMe_2$ | CONHCOPh | $5,6Cl_2$ | 183-5 |
| 25 | $NMe_2$ | COMe | $5/6Cl$ | 156-8 |
| 26 | $NMe_2$ | CONHSO$_2$—⟨⟩—Cl | $5,6Cl_2$ | 174 |
| 27 | $NMe_2$ | H | $5NO_2$ | 169-71 |
| 28 | $NMe_2$ | H | $6NO_2$ | 171-2 |

Notes
*7-aza means the CH in the ring is replaced by N
In the column headed $(W)_n$, 5/6 indicates that the compound exists as a mixture of the 5- and 6-substituted isomers; similarly compound 10 is a mixture of the two isomers shown.
The starting materials for compounds 6 and 8 are novel compounds which were prepared in known manner by reacting the 5,6,7-trihalo-benzimidazole-2-carbonitrile with dimethylsulphamoyl chloride and then using them without purification.

EXAMPLE 7

Sodium hydride (80% in oil; 0.39 g) was added portionwise to a stirred solution of 5,6-dichlorobenzimidazole-2-carbonitrile (2.74 g) in dry 1,2-dimethoxyethane (40 ml) with ice-bath cooling. After the effervescence had ceased, tetramethylphosphorodiamidic chloride (2.20 g) was added to the resulting clear solution and the mixture stirred and heated under reflux for 6 h with exclusion of atmospheric moisture. The mixture was evaporated to dryness in vacuo and the residue redissolved in dichloromethane (75 ml) and the solution filtered. The filtrate was evaporated to dryness and the residue recrystallised from cyclohexane to give 5,6-dichloro-1-[bis(dimethylaminophosphinyl)]benzimidazole-2-carbonitrile, m.p. 121-3. (Compound 29).

This was treated with hydrogen sulphide in a similar manner to that described in Example 1, to give 5,6-dichloro-1-[bis(dimethylaminophosphinyl)]benzimidazole-2-carbothioamide, m.p. 146-7. (Compound 30).

EXAMPLE 8

The compounds of the invention were assessed for activity against the following:
*Phytophthora infestans:* early blight of tomatoes (PI)
*Plasmopara viticola:* vine downy mildew (PV)

The compounds are formulated in aqueous acetone with Tween 20 wetter to give a concentration of 500 ppm compound/125 ppm wetter/20,000 ppm acetone. Plants are then treated with the diluted suspensions and then inoculated, 24 hours after treatment with test compound, by spraying with spore suspensions of the fungi and then incubating in a humid atmosphere: >98% RH, as summarised in Table 1.

TABLE 1

| Pathogen | Incubation time (days) | Temperature day | Temperature night | Light conditions | Duration of high humidity days |
|---|---|---|---|---|---|
| *P. infestans* | 4 | 14 | 10 | 17 hrs light/ 7 hrs dark per day | 1 |
| *P. viticola* | 11 | 18 | 14 | 16 hrs light/ 8 hrs dark per day | 11 |

After the appropriate period of incubation, the degree of infection of the leaf surface is visually estimated.

Compounds are considered active if they give greater than 50% control of the disease at a concentration of 500 ppm (w/v) or less. Compounds 1–27, 29 and 30 were active against these two pathogens and compound 28 was active against the second.

In a similar test, the activity of compounds of the invention against *Phytophthora infestans* were compared with 5,6-dichloro-benzimidazole-2-carbonitrile (compound 14 in GB No. 2114567). Five replicates were used at each dose. The results are as follows;

| Compound No | % Control Rate(ppm) 2.5 | 1.25 |
|---|---|---|
| 1 | 97 | 88 |
| 2 | 98 | 99 |
| 5 | 99 | 96 |
| 3 | 96 | 99 |
| 8 | 100 | 100 |
| 12 | 100 | 98 |
| Comparison compound | 97 | 77 |

EXAMPLE 6

This example illustrates a typical concentrate that can be formulated from compounds of the invention.

| Wettable powder | |
|---|---|
| Compound of the invention | 25% w/w |
| Sodium lignosulphonate | 5% w/w |
| China clay | 70% w/w |

We claim:

1. A compound of formula I

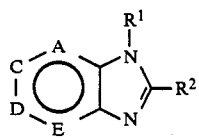

(I)

where at least three of A, C, D and E are —CX= and the other is —CX= or —N=, where X is hydrogen, $C_{1-8}$-alkyl (optionally substituted by halogen), halo, nitro or phenoxy, in which the phenyl is optionally substituted by one or more groups selected from halo and trifluoromethyl;

$R^1$ is —SO$_2$R$^3$ or

and
$R^2$ is

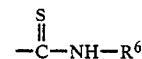

where $R^6$ is hydrogen, $C_{1-8}$-alkyl (optionally substituted by one or more groups selected from halogen and hydroxy), $C_{1-8}$-alkanoyl, benzoyl, cyclohexylcarbonyl or aminocarbonyl (in which the amino is substituted by benzoyl or chlorobenzenesulphonyl);

$R^3$, $R^4$, and $R^5$ may be the same or different and have the meanings given to $R^6$ or can be di-$C_{1-8}$-alkylamino; and Z is oxygen or sulphur;

and when $R^1$ is

$R^2$ can also be —CN.

2. A compound according to claim 1, in which all of the A, C, D and E groups are —CX=.

3. A compound according to claim 2, in which $R^1$ is —SO$_2$NMe$_2$ and $R^2$ is CSNH$_2$.

4. A fungicidal composition comprising a fungicidally effective amount of a compound as claimed in claim 1 in admixture with an agriculturally acceptable diluent or carrier.

5. A fungicidal composition comprising a fungicidally effective amount of a compound as claimed in claim 2 in admixture with an agriculturally acceptable diluent or carrier.

6. A fungicidal composition comprising a fungicidally effective amount of a compound as claimed in claim 3 in admixture with an agriculturally acceptable diluent or carrier.

7. A fungicidal emulsifiable concentrate comprising a compound as claimed in claim 1 in admixture with an agriculturally acceptable diluent or carrier.

8. A fungicidal emulsifiable concentrate comprising a compound as claimed in claim 2 in admixture with an agriculturally acceptable diluent or carrier.

9. A fungicidal emulsifiable concentrate comprising a compound as claimed in claim 3 in admixture with an agriculturally acceptable diluent or carrier.

10. A method of combating fungi at a locus infested or liable to be infested therewith, which comprises applying to the locus a fungicidally effective amount of a compound as claimed in claim 1.

11. A method of combating fungi at a locus infested or liable to be infested therewith, which comprises applying to the locus a fungicidally effective amount of a compound as claimed in claim 2.

12. A method of combating fungi at a locus infested or liable to be infested therewith, which comprises applying to the locus a fungicidally effective amount of a compound as claimed in claim 3.

* * * * *